(12) United States Patent
Tadele et al.

(10) Patent No.: US 11,744,476 B2
(45) Date of Patent: Sep. 5, 2023

(54) BLOOD PRESSURE MEASUREMENT USING DEVICE WITH PIEZOELECTRIC SENSOR

(71) Applicant: Apple Inc., Cupertino, CA (US)

(72) Inventors: Wegene H. Tadele, San Francisco, CA (US); Makiko K. Brzezinski, San Jose, CA (US); Riley E. Brandt, Menlo Park, CA (US); Siddharth Nangia, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 248 days.

(21) Appl. No.: 16/998,902

(22) Filed: Aug. 20, 2020

(65) Prior Publication Data

US 2022/0054020 A1 Feb. 24, 2022

(51) Int. Cl.
*A61B 5/025* (2006.01)
*A61B 5/022* (2006.01)
(Continued)

(52) U.S. Cl.
CPC .......... *A61B 5/025* (2013.01); *A61B 5/02108* (2013.01); *A61B 5/02141* (2013.01);
(Continued)

(58) Field of Classification Search
CPC ................ A61B 5/025; A61B 5/02108; A61B 5/02141; A61B 5/02225; A61B 5/02233;
(Continued)

(56) References Cited

U.S. PATENT DOCUMENTS

| 4,896,676 A | 1/1990 | Sasaki |
|---|---|---|
| 5,135,003 A | 8/1992 | Souma |

(Continued)

FOREIGN PATENT DOCUMENTS

| CN | 103598879 | 2/2014 |
|---|---|---|
| CN | 110301906 | 10/2019 |

(Continued)

OTHER PUBLICATIONS

Horsey, "Yhe smartwatch wearable blood pressure monitor," geeky-gadgets.com/wearable-blood-pressure-monitor-07-02-2020, Feb. 7, 2020, 3 pages.

(Continued)

*Primary Examiner* — Eric F Winakur
*Assistant Examiner* — Jonathan Drew Moroneso
(74) *Attorney, Agent, or Firm* — Brownstein Hyatt Farber Schreck, LLP

(57) ABSTRACT

A blood pressure measurement device may include one or more piezoelectric sensors (e.g., differential piezoelectric sensors) for detecting blood flow through a limb of a user as part of determining blood pressure measurements. The piezoelectric sensor(s) may additionally or alternatively be used to determine one or more biological parameters of users (e.g., a ballistocardiogram, a heart rate, a heart rate variability, and a pulse wave velocity). The blood pressure measurement device may additionally or alternatively include a capacitive sensor for determining a pressure applied to the limb of the user by the blood pressure measurement device and/or operational states of the blood pressure measurement devices (off-arm, on-arm, inflating, deflating, tightness, and the like).

14 Claims, 10 Drawing Sheets

(51) Int. Cl.
  *A61B 5/021* (2006.01)
  *A61B 5/00* (2006.01)
  *A61B 5/024* (2006.01)

(52) U.S. Cl.
  CPC ...... *A61B 5/02225* (2013.01); *A61B 5/02233* (2013.01); *A61B 5/02405* (2013.01); *A61B 5/7225* (2013.01)

(58) Field of Classification Search
  CPC .... A61B 5/02405; A61B 5/7225; A61B 5/022
  See application file for complete search history.

(56) References Cited

U.S. PATENT DOCUMENTS

| | | | |
|---|---|---|---|
| 6,162,181 | A | 12/2000 | Hynson et al. |
| 6,497,668 | B2 | 12/2002 | Nishibayashi |
| 6,689,069 | B2 | 2/2004 | Bratteli et al. |
| 6,694,821 | B2 | 2/2004 | Yamakoshi et al. |
| 7,678,059 | B2 | 3/2010 | Friedman et al. |
| 8,690,799 | B2 | 4/2014 | Telfort et al. |
| 8,998,817 | B2 | 4/2015 | Pfeiffer et al. |
| 9,192,351 | B1 | 11/2015 | Telfort et al. |
| 9,198,584 | B2 | 12/2015 | Yamashita et al. |
| 9,986,919 | B2 | 6/2018 | Lamego et al. |
| 10,064,561 | B2 | 9/2018 | Kinoshita et al. |
| 10,405,806 | B2 | 9/2019 | Baik et al. |
| 11,134,901 | B2 | 10/2021 | Fine et al. |
| 11,172,839 | B2 | 11/2021 | Ward et al. |
| 11,298,032 | B2 | 4/2022 | Mou et al. |
| 11,576,583 | B2 | 2/2023 | Dana et al. |
| 2006/0111637 | A1 | 5/2006 | Jacober et al. |
| 2007/0203416 | A1* | 8/2007 | Lowe ............... A61B 5/02233 600/485 |
| 2008/0234589 | A1* | 9/2008 | Riobo Aboy ....... A61B 5/0225 600/490 |
| 2009/0012411 | A1 | 1/2009 | Lowe et al. |
| 2010/0106029 | A1 | 4/2010 | Fraden |
| 2012/0136262 | A1 | 5/2012 | Sawanoi et al. |
| 2012/0209129 | A1 | 8/2012 | Smith et al. |
| 2013/0060147 | A1* | 3/2013 | Welch ............... A61B 5/02208 600/479 |
| 2013/0144176 | A1 | 6/2013 | Lec |
| 2014/0187987 | A1 | 7/2014 | Fraden et al. |
| 2014/0309541 | A1 | 10/2014 | Yamashita et al. |
| 2015/0105675 | A1* | 4/2015 | Nakagawa ......... A61B 5/02125 600/493 |
| 2016/0038044 | A1 | 2/2016 | Banerjee et al. |
| 2016/0106326 | A1 | 4/2016 | Bajaj et al. |
| 2016/0120418 | A1 | 5/2016 | Oksala et al. |
| 2017/0273579 | A1 | 9/2017 | Mori et al. |
| 2017/0290519 | A1 | 10/2017 | Zhou |
| 2018/0184920 | A1* | 7/2018 | Rabinovich ......... A61B 5/0205 |
| 2018/0206746 | A1* | 7/2018 | Narasimhan ......... A61B 5/0225 |
| 2018/0338693 | A1 | 11/2018 | Li et al. |
| 2019/0261870 | A1 | 8/2019 | Nishikawa |
| 2020/0323446 | A1 | 10/2020 | Nishida et al. |
| 2021/0059537 | A1 | 3/2021 | Nakagawa et al. |
| 2021/0127993 | A1 | 5/2021 | Matsumura et al. |
| 2021/0169347 | A1 | 6/2021 | Ito et al. |
| 2021/0236012 | A1 | 8/2021 | Nishida et al. |
| 2021/0251499 | A1 | 8/2021 | Ogawa |
| 2021/0321889 | A1 | 10/2021 | Jain et al. |
| 2022/0000380 | A1* | 1/2022 | Li ..................... A61B 5/742 |
| 2022/0015652 | A1 | 1/2022 | Lee et al. |
| 2022/0054020 | A1 | 2/2022 | Tadele et al. |
| 2022/0087545 | A1 | 3/2022 | Jain et al. |
| 2022/0400959 | A1 | 12/2022 | Montgomery et al. |
| 2023/0063813 | A1 | 3/2023 | Smith et al. |
| 2023/0068620 | A1 | 3/2023 | Tadele et al. |

FOREIGN PATENT DOCUMENTS

| | | |
|---|---|---|
| JP | 3120617 U | 3/2006 |
| JP | 3121082 U | 4/2006 |
| WO | WO 11/023343 | 3/2011 |
| WO | WO 20/016139 | 1/2020 |

OTHER PUBLICATIONS

U.S. Appl. No. 17/354,775, filed Jun. 22, 2021, Montgomery II et al.
U.S. Appl. No. 17/398,775, filed Aug. 10, 2021, Jain et al.
U.S. Appl. No. 16/928,933, filed Jul. 14, 2020, Lee et al.
U.S. Appl. No. 17/166,914, filed Feb. 3, 2021, Han et al.
U.S. Appl. No. 17/210,371, filed Mar. 23, 2021, Jain et al.

* cited by examiner

BLOOD PRESSURE MEASUREMENT USING DEVICE WITH PIEZOELECTRIC SENSOR

FIELD

Embodiments relate generally to devices and methods for determining blood pressure measurements. More particularly, the described embodiments relate to blood pressure measurement devices having one or more piezoelectric sensors for performing blood pressure measurements.

BACKGROUND

Many traditional devices for determining blood pressure use audio sensors (e.g., microphones) to detect audio signals related to blood flow through blood vessels. Audio sensors may be capable of receiving audio signals at a relatively small area of a user's limb, and accordingly, traditional blood pressure devices may be highly sensitive to where they are placed and prone to errors.

SUMMARY

Embodiments of the systems, devices, methods, and apparatuses described in the present disclosure are directed to blood pressure measurement devices having one or more piezoelectric sensors for determining blood pressure measurements.

One embodiment may take the form of a blood pressure measurement device that includes a cuff configured to extend around an arm of a user. The cuff may include an inflatable bladder. The blood pressure measurement device may further include a pump configured to inflate the inflatable bladder to occlude a blood vessel of the user. The blood pressure measurement device may further include a piezoelectric sensor coupled to the cuff and configured to detect blood flow through the arm of the user and output a first signal corresponding to the blood flow. The blood pressure measurement device may further include a capacitive sensor coupled to the inflatable bladder and configured to provide a second signal corresponding to a pressure applied to the arm of the user by the cuff and a processing unit operably coupled to the piezoelectric sensor and configured to determine a blood pressure of the user using the first signal and the second signal.

Another embodiment may take the form of a blood pressure measurement device that includes a cuff comprising an inflatable bladder. The blood pressure measurement device may further include a processing unit configured to cause the inflatable bladder to inflate to an inflated state. The cuff may be configured to occlude an artery of a user when the inflatable bladder is in the inflated state. The processing unit may be further configured to cause the inflatable bladder to deflate during a deflation sequence. The blood pressure measurement device may further include a differential polyvinylidene fluoride (PVDF) sensor coupled to the inflatable bladder and configured to output a signal during the deflation sequence, the signal corresponding to blood flow through the artery. The processing unit may be further configured to filter the signal to isolate an oscillometric waveform and a biological waveform, analyze the oscillometric waveform to determine at least one of a systolic blood pressure, a diastolic blood pressure, or a mean arterial pressure, and analyze the biological waveform to determine a biological parameter of the user.

Another embodiment may take the form of a blood pressure measurement device that includes a bladder section that includes a first flexible layer and a second flexible layer coupled to the first flexible layer to form an inflatable interior volume between the first flexible layer and the second flexible layer. The blood pressure measurement device may further include a first differential polyvinylidene fluoride (PVDF) sensor coupled to the first flexible layer and configured to output a first signal corresponding to blood flow through an arm of a user and a second differential PVDF sensor coupled to the first flexible layer to output a second signal corresponding to the blood flow through the arm of the user. The blood pressure measurement device may further include a processing unit operably coupled to the first and second differential PVDF sensors and configured to determine a blood pressure of the user using the first signal and the second signal.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1:
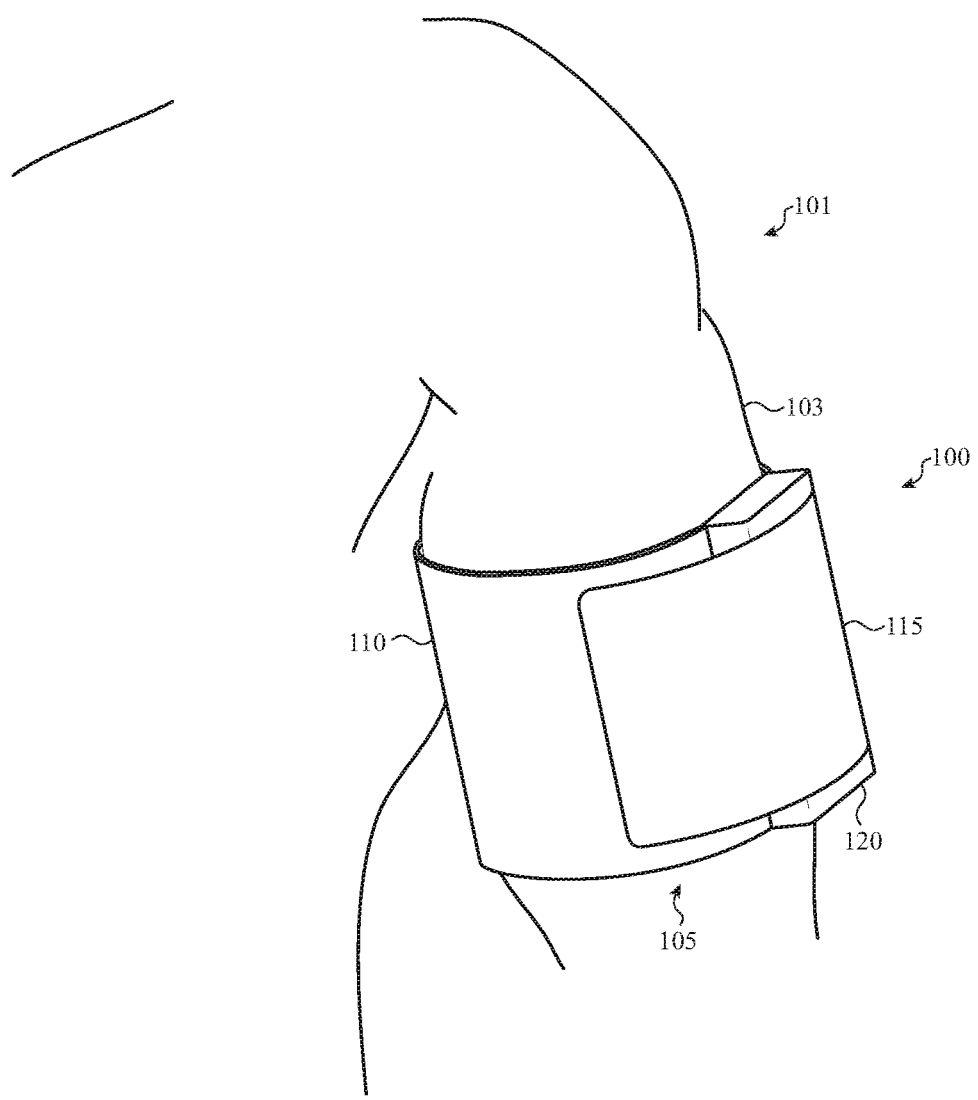
FIG. 1 illustrates an example blood pressure measurement device as worn by a user.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to devices for determining blood pressure measurements and other biological parameters. The blood pressure measurement devices may include one or more piezoelectric sensors (e.g., differential piezoelectric sensors) for detecting blood flow through limbs of users as part of determining blood pressure measurements. In some cases, the piezoelectric sensors may additionally or alternatively be used to determine one or more biological parameters of users (e.g., a ballistocardiogram, a heart rate, a heart rate variability, and a pulse wave velocity).

The blood pressure measurement devices described herein may include one or more capacitive sensors for detecting a pressure applied to the arm of the user by the blood pressure measurement devices and/or operational states of the blood pressure measurement devices (off-arm, on-arm, inflating, deflating, and the like).

The blood pressure measurement devices described herein may include a cuff that extends around a limb (e.g., an arm or a leg) of a user. The cuff may include an inflatable bladder, and when the inflatable bladder is in an inflated state, the cuff may occlude one or more blood vessels (e.g., veins, arteries, etc.) of the user. The piezoelectric sensor and/or the capacitive sensor may be coupled to the inflatable bladder or elsewhere along the cuff.

The blood pressure measurement devices described herein may include a processing unit that causes the inflatable bladder to inflate to the inflated state. The air pressure within the inflatable bladder in the inflated state, and therefore the pressure exerted on the arm by the cuff may vary for different users. In some cases, the air pressure in the inflated state may be determined based on an estimation of a systolic blood pressure of the user, and so it may differ based on different estimated systolic blood pressures. The processing unit may cause the inflatable bladder to deflate during a deflation sequence in which air is gradually released from the inflatable bladder to reduce the pressure exerted on the arm by the cuff.

The piezoelectric sensor may be used to detect blood flow through the limb of the user during the deflation sequence, and output signals corresponding to the blood flow. The signals output by the piezoelectric sensor may correspond to vibrations, sounds, or other disturbances resulting from changes in the blood flow through vessels in the limb as the pressure exerted on the arm by the cuff changes. In some cases, the signal output by a piezoelectric sensor during a deflation sequence includes an oscillometric waveform corresponding to arterial pressure changes within the artery of the user. In some cases, the signal output by a piezoelectric sensor during a deflation sequence includes sounds (e.g., Korotkoff sounds) corresponding to turbulent flow through a partially-occluded artery.

The capacitive sensor may output a pressure signal corresponding to the pressure applied to the arm of the user during the deflation process. The processing unit may correlate the oscillometric waveform and/or the sounds present in the signal output by the piezoelectric sensor to the pressure signal to determine estimated blood pressure measurements. The processing unit may determine an oscillometric blood pressure measurement, which may include determining an estimated mean arterial pressure corresponding to the value of the pressure applied to the arm during a peak oscillation of the oscillometric waveform. Additionally or alternatively, the processing unit may determine an auscultatory blood pressure measurement, which may include determining an estimated systolic blood pressure corresponding to the value of the pressure applied to the arm when a first Korotkoff sound is detected, and/or an estimated diastolic blood pressure corresponding to the value of the blood pressure applied to the arm when a final Korotkoff sound is detected.

In some cases, the signal output by the piezoelectric sensor may be used to determine estimated blood pressure measurements using both oscillometric and auscultatory methods. The processing unit may filter the signal output by the piezoelectric sensor to isolate the oscillometric waveform and/or the Korotkoff sounds as part of determining oscillometric and/or auscultatory blood pressure measurements.

In some cases, the blood pressure measurement device may be used to determine one or more biological parameters in addition to or instead of determining a blood pressure measurement. Biological parameters may include a ballistocardiogram, a heart rate, a heart rate variability, or a pulse wave velocity, and the like. In various embodiments, the signals output by the piezoelectric sensor may include biological waveforms corresponding to biological parameters. The processing unit may filter the signals output by the piezoelectric sensor to isolate the biological waveforms, which may then be used to determine the biological parameters. In some cases, the blood pressure measurement device may include one or more additional or alternative sensors for detecting signals for determining biological parameters.

Additionally or alternatively, the blood pressure measurement device may be used to determine one or more operational states of the blood pressure monitoring device. The operational states of the blood pressure monitoring device may include an on-arm or off-arm state, a tightness of the blood pressure monitoring device around a user's limb, and the like. An output signal of the sensor may correspond to the operational state of the blood pressure monitoring device. In various embodiments, the piezoelectric sensor(s) may be used to determine operational states of the blood pressure monitoring device. In some cases, the blood pressure measurement device may include one or more additional or alternative sensors for determining operational states.

The blood pressure measurement devices described herein may provide numerous advantages over traditional devices. In particular, the piezoelectric sensors described herein may be used to perform multiple measurements simultaneously, including oscillometric blood pressure measurements, auscultatory blood pressure measurements, and biological parameter measurements. These time-synchronized measurements may be useful for verifying measurement accuracy and/or providing additional useful data for diagnostic and informational purposes. Traditional devices may use multiple discrete sensors of different types to perform these measurements. For example, auscultatory blood pressure measurements may be performed using MEMS microphones, while oscillometric blood pressure measurements may use multiple discrete pressure sensors. The embodiments described herein may allow a single sensor to perform one or more of these measurements, which simplifies the device, thereby reducing cost and manufacturing complexity.

The term "attached," as used herein, may be used to refer to two or more elements, structures, objects, components, parts or the like that are physically affixed, fastened, and/or retained to one another. The term "coupled," as used herein, may be used to refer to two or more elements, structures, objects, components, parts or the like that are physically attached to one another, operate with one another, communicate with one another, are in electrical connection with one another, and/or otherwise interact with one another. Accordingly, while elements attached to one another are coupled to one another, the reverse is not required. As used herein, "operably coupled" or "electrically coupled" may be used to refer to two or more devices that are coupled in any suitable manner for operation and/or communication, including wiredly, wirelessly, or some combination thereof. As used herein, the term "abutting" means that two elements share a common boundary or otherwise contact one another, while the term "adjacent" means that two elements are near one another and may (or may not) contact one another. Thus, elements that are abutting are also adjacent, although the reverse is not necessarily true.

These and other embodiments are discussed with reference to FIGS. 1-10. However, those skilled in the art will readily appreciate that the detailed description given herein with respect to these figures is for explanatory purposes only and should not be construed as limiting.

FIG. 1 illustrates an example blood pressure measurement device 100 as worn by a user 101. The blood pressure measurement device 100 can include a cuff 105 that wraps around a limb 103 (e.g., an arm or a leg) of a user 101. The cuff 105 may include a bladder section 110 that extends the entire length of the cuff 105. Alternatively, the bladder section 110 may extend part of the length of the cuff 105, and the cuff may include a non-inflatable section 115 in addition to the bladder section 110. The bladder section 110 and the non-inflatable section 115 can wrap around the limb 103 of the user 101 such that the cuff 105 encircles the limb 103. The blood pressure measurement device 100 can also include a control module 120 that is coupled to the cuff 105.

The bladder section 110 may define an inflatable bladder that inflates to an inflated state, which tightens the blood pressure measurement device 100 around the limb 103. The inflatable bladder may extend at least partially around the limb 103 (e.g., an arm) of the user. This may result in the cuff 105 occluding one or more blood vessels (e.g., arteries, veins, etc.) in the limb 103 to perform blood pressure measurements. As used herein, "occluding" a blood vessel may refer to restricting (e.g., partially compressing) or closing (e.g., completely compressing) the blood vessel such that blood flow through the blood vessel is reduced or ceased.

Figure 2:
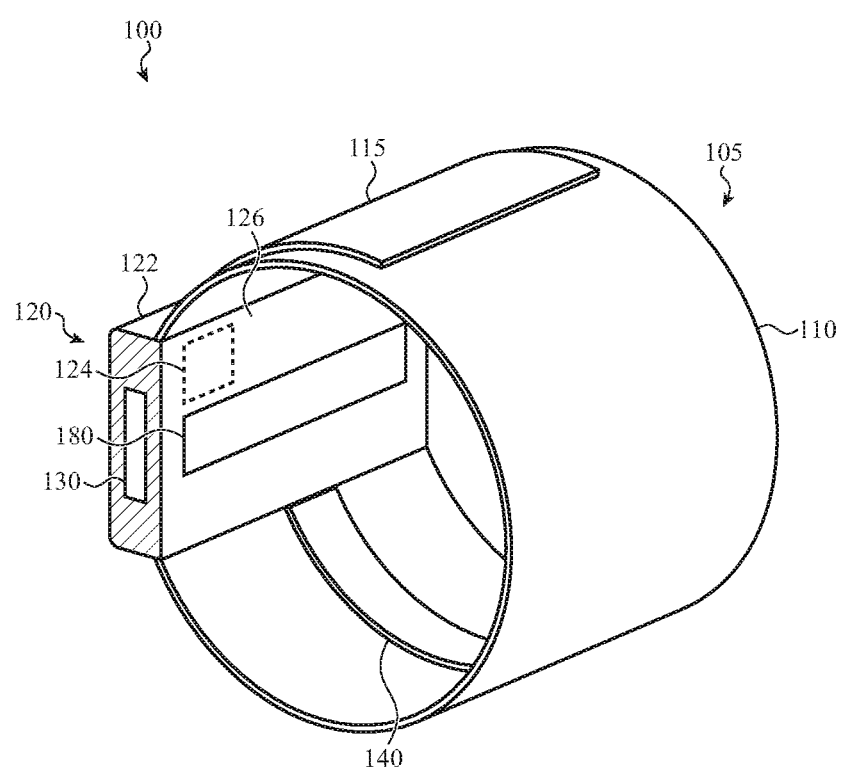
FIG. 2 illustrates the example blood pressure measurement device of FIG. 1 in a closed configuration.

FIG. 2 illustrates the example blood pressure measurement device 100 in a closed configuration as it would be worn by a user. The control module 120 can include components that are used to take a blood pressure measurement. The inflatable bladder may be inflated to an inflated state and then deflated during a deflation sequence during a blood pressure measurement process.

The control module 120 may include or be operably coupled to a processing unit 124 that causes the inflatable bladder to inflate to the inflated state. The inflatable bladder may be inflated to an inflated state to occlude one or more arteries in the limb 103. The control module 120 may include an air pump 130 for inflating the inflatable bladder defined by the bladder section 110. The air pump 130 may inflate the inflatable bladder by introducing pressurized air into the inflatable interior volume of the inflatable bladder in response to receiving an instruction or signal (e.g., a voltage level) from the processing unit. The air pressure within the inflatable bladder in the inflated state, and therefore the pressure exerted on the limb 103 by the cuff 105 may vary for different users. In some cases, the air pressure in the inflated state may be determined based on an estimation of a systolic blood pressure of the user, and so it may differ based on different estimated systolic blood pressures.

The processing unit 124 may cause the inflatable bladder to deflate during a deflation sequence in which air is gradually released from the inflatable bladder to reduce the pressure exerted on the limb 103 by the cuff 105. In various embodiments, the piezoelectric sensor 140 may detect signals during the deflation sequence to perform a blood pressure measurement. In some cases, the air pump 130 is used to deflate the inflatable bladder. Additionally or alternatively, the blood pressure measurement device 100 may include one or more valves for inflating and/or deflating the inflatable bladder.

The blood pressure measurement device 100 may include a piezoelectric sensor 140 coupled to the bladder section 110. The piezoelectric sensor 140 may be used to detect signals for performing blood pressure measurements during the deflation sequence and/or at other times. The signals detected by the piezoelectric sensor 140 may correspond to vibrations, sounds, or other disturbances resulting from changes in the blood flow through vessels in the limb 103 as the pressure exerted on the arm by the cuff 105 changes. In some cases, the signal output by a piezoelectric sensor during a deflation sequence includes an oscillometric waveform corresponding to arterial pressure changes within the artery of the user. In some cases, the signal output by a piezoelectric sensor during a deflation sequence includes sounds (e.g., Korotkoff sounds) corresponding to turbulent flow through a partially-occluded artery. The piezoelectric sensor 140 may be a differential polyvinylidene fluoride (PVDF) sensor, as discussed in more detail below with respect to FIGS. 5A-6.

The blood pressure measurement device 100 may additionally or alternatively include a capacitive sensor 180 for detecting the pressure applied to the limb 103 by the cuff 105. The capacitive sensor 180 may output a pressure signal corresponding to the pressure applied to the arm of the user during the deflation process. The processing unit 124 may correlate signals or waveforms detected by the piezoelectric sensor 140 (e.g., the oscillometric waveform and/or the sounds present in the signal output by the piezoelectric sensor 140) to the pressure signal to determine estimated blood pressure measurements, as discussed in more detail below with respect to FIG. 3.

The capacitive sensor 180 may use mutual-capacitive sensing techniques and/or self-capacitive sensing techniques. In some cases, the capacitive sensor 180 includes electrodes coupled to opposite sides of a sensing substrate and further coupled to a differential sensor (e.g., a differential sense amplifier). A capacitance between the electrodes may correspond to the pressure exerted on the limb 103 by the cuff 105. The capacitive sensor 180 may be positioned along a back plate 126 of the control module 120 or at any suitable location of the blood pressure monitoring device 100. Additionally or alternatively, the capacitive sensor 180 may be coupled to the cuff 105 (e.g., a flexible layer of the bladder section). In various embodiments, the capacitive sensor 180 may also be used to detect operational states of the blood pressure measurement device 100 (off-arm, on-arm, inflating, deflating, and the like), as described in more detail below with respect to FIG. 9.

In some cases, the pressure signals output by the capacitive sensor 180 may be direct current (DC) signals (e.g., signals that do not oscillate), while the signals output by the piezoelectric sensor 140 may be alternating current (AC) signals (e.g., signals that oscillate). In various embodiments, the signals output by the capacitive sensor 180 and the piezoelectric sensor 140 may consist of AC signals, DC signals, or both. In some cases, the capacitive sensor 180 may be omitted, and the signals output by the piezoelectric sensor 140 may be used to determine the pressure applied to the limb 103 of the user during the deflation process. For example, the processing unit 124 may filter the signal output by the piezoelectric sensor 140 to isolate a pressure waveform corresponding to the pressure applied to the limb 103 of the user during the deflation process.

The control module 120 may include one or more other components not shown in FIG. 1, such as a memory, a battery, and so on that are used to perform blood pressure measurements. Additionally or alternatively, the blood pressure measurement device 100 may be operably coupled to one or more devices having a processing unit, memory, a battery, and so on that are used to perform blood pressure measurements. The piezoelectric sensor 140 may be operably coupled to the control module 120 such that a processing unit of the control module 120 or otherwise operably coupled to the piezoelectric sensor 140 may receive the signals detected by the piezoelectric sensor and determine a blood pressure of the user 101 using the signals.

The control module 120 may include a housing 122 that encloses one or more components of the control module. The housing 122 may be coupled to the cuff 105. In some cases, the housing 122 is coupled to the bladder section 110 of the blood pressure measurement device 100.

Figure 3:
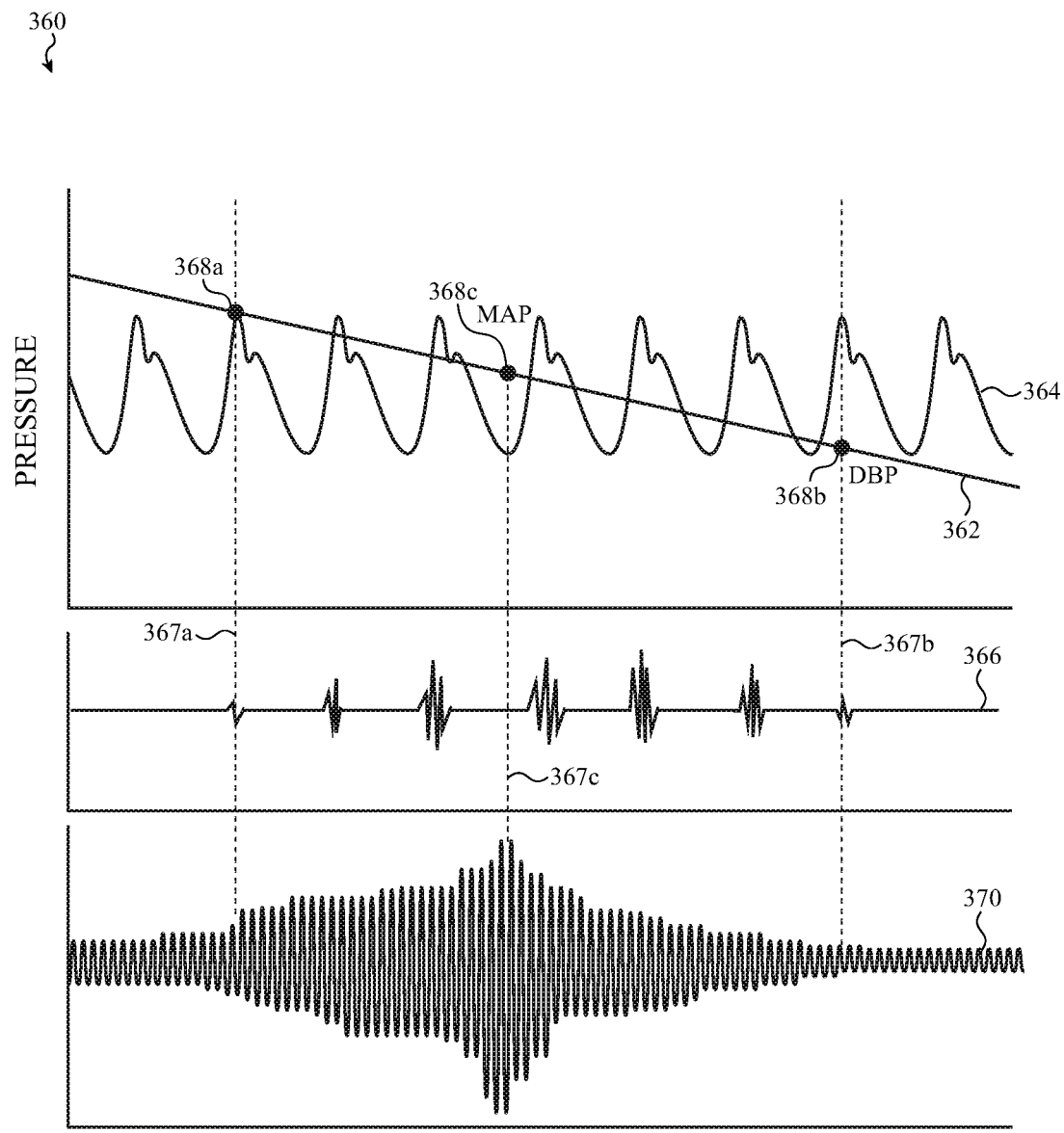
FIG. 3 is a chart that illustrates how isolated waveforms may be correlated to a pressure signal to determine oscillometric and/or auscultatory blood pressure measurements.

As noted above, oscillometric and/or sound waveforms from the signal output by the piezoelectric sensor 140 may be correlated to the pressure signal detected by the capacitive sensor 180, the piezoelectric sensor, or another pressure sensor to determine estimated blood pressure measurements. FIG. 3 is a chart 360 that illustrates how isolated waveforms may be correlated to a pressure signal 362 to determine oscillometric and/or auscultatory blood pressure measurements. The pressure signal 362 may be determined using a capacitive sensor (e.g., capacitive sensor 180), another pressure sensor, and/or by filtering the signal output by the piezoelectric sensor 140. FIG. 3 illustrates an example true blood-pressure waveform 364, representing the actual fluctuation of blood pressure attributable to a user's heartbeats for purposes of illustration. As shown in FIG. 3, a systolic blood pressure value 368a corresponds to a peak of the true blood-pressure waveform 364, and a diastolic blood pressure value 368b corresponds to a trough of the true blood-pressure waveform 364.

The pressure signal 362 shows a deflation sequence of the inflatable bladder in which blood pressure measurements may be taken. As noted above, the processing unit 124 may filter and/or perform analysis on the signal output by the piezoelectric sensor 140 to isolate the oscillometric waveform and/or the sound waveforms as part of determining oscillometric and/or auscultatory blood pressure measurements. For example, Korotkoff sounds may be detected in a higher frequency band than pressure changes occurring in the blood volume. Accordingly, the signal output by the piezoelectric sensor 140 can be filtered using a high frequency band pass filter to isolate a sound signal 366 corresponding to sound events (e.g., Korotkoff sounds) occurring due to changes in the blood flow. Additionally or alternatively, the signal output by the piezoelectric sensor 140 can be filtered using a low frequency band pass filter to isolate an oscillometric signal 370 corresponding to pressure changes occurring in the blood volume. The sound signal 366 may be used to determine an auscultatory blood pressure measurement. Additionally or alternatively, the oscillometric signal 370 may be used to determine an oscillometric blood pressure measurement.

To determine an auscultatory blood pressure measurement using the sound signal 366, the processing unit 124 may determine the pressure applied to the limb 103 when a first sound 367a (e.g., the first Korotkoff sound of a sequence) is detected, which may correspond to an estimated systolic blood pressure value 368a. Additionally or alternatively, the processing unit 124 may determine the pressure applied to the limb 103 when a subsequent sound 367b (e.g., the last Korotkoff sound of a sequence) is detected, which may correspond to an estimated diastolic blood pressure value 368b.

To determine an oscillometric blood pressure measurement using the oscillometric signal 370, the processing unit 124 may determine the pressure applied to the limb 103 corresponding to a peak 367c (e.g., a maximum oscillation) of the oscillometric signal 370. This pressure may correspond to an estimated mean arterial pressure 368c. The processing unit 124 may determine estimated systolic and diastolic blood pressure values 368a, 368b using the mean arterial pressure 368c.

Additionally or alternatively, the oscillometric signal 370 or another signal isolated from the signal output by the piezoelectric sensor 140 may be used to determine one or more biological parameters of the user. Biological parameters may include a ballistocardiogram, a heart rate, a heart rate variability, or a pulse wave velocity, and the like. In various embodiments, the signals output by the piezoelectric sensor 140 may include biological waveforms corresponding to biological parameters. The processing unit 124 may filter and/or analyze the signals output by the piezoelectric sensor to isolate the biological waveforms, which may then be used to determine the biological parameters. For example, the signal output by the piezoelectric sensor 140 can be filtered using a low frequency band pass filter to isolate a biological waveform. In some cases, the blood pressure measurement device 100 may include one or more additional or alternative sensors for detecting signals for determining biological parameters.

Figure 4:
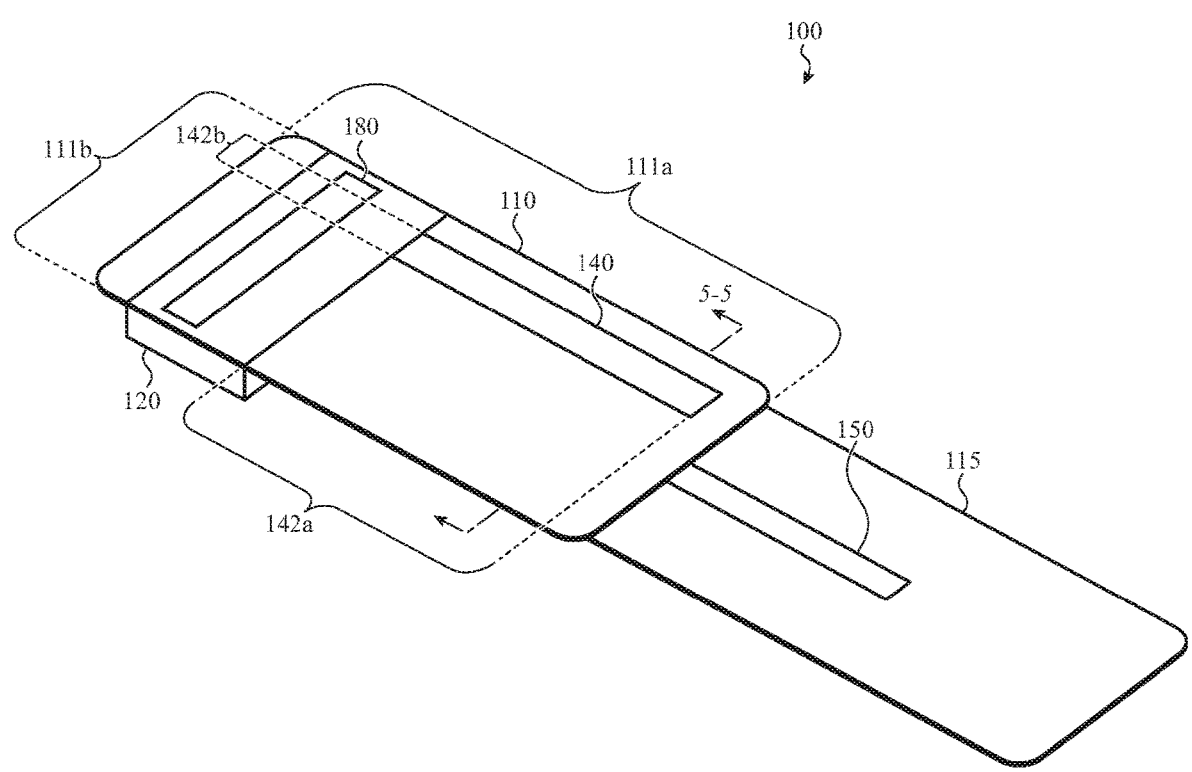
FIG. 4 illustrates the example blood pressure measurement device of FIG. 1 in an open configuration.

FIG. 4 illustrates the example blood pressure measurement device 100 in an open configuration. In some cases, the bladder section 110 may extend the entire length of the cuff 105. In some cases, as shown in FIG. 4, the bladder section 110 may extend part of the length of the cuff 105, and the cuff may include a non-inflatable section 115 in addition to the bladder section 110.

The cuff 105 can be wrapped around the limb 103 and the first and second ends can be coupled by a fastening mechanism 150. In some examples, the fastening mechanism 150 can include any suitable mechanism that secures the first and second ends of the cuff 105 together while the cuff is being worn by the user 101. The fastening mechanism 150 may include one or more materials or components located in different areas on the bladder section 110 and/or the non-inflatable section 115. Examples of fastening mechanisms 150 can include hook-and-loop fasteners, clips, zippers, buttons, and so on. In some examples, the first and second ends of the cuff 105 can be permanently joined and the cuff 105 can be placed on the limb 103 by a user 101 sliding their limb through a central opening define by the cuff 105.

As shown in FIG. 4, the cuff 105 and/or the bladder section 110 may have an elongated shape. The bladder section 110 may define a length 111a and a width 111b less than the length 111a. The length 111a of the bladder section 110 may extend circumferentially around the limb of the user 101. Said another way, the length 111a of the bladder section 110 may extend at least partially around a circumference of an arm of the user.

The piezoelectric sensor 140 may have an elongated shape. The piezoelectric sensor 140 may define a length 142a and a width 142b less than the length 142a. The length 142a of the piezoelectric sensor 140 may be configured to extend circumferentially around the limb of the user 101. Said another way, the length 142a of the piezoelectric sensor 140 may extend at least partially around a circumference of an arm of the user.

The length 142a of the piezoelectric sensor may extend parallel to the length 111a of the bladder section 110. This may allow the piezoelectric sensor 140 to extend at least partially around the limb 103 of the user 101. Additionally or alternatively, the length 142a of the piezoelectric sensor 140 may extend parallel to the width 111b of the bladder section 110, as shown and described with respect to FIG. 7.

The piezoelectric sensor 140 may be formed of or include a flexible piezoelectric material so that the cuff 105 may remain flexible to extend around a user's limb. Examples of flexible piezoelectric materials include polyvinylidene fluoride (PVDF), polyvinylidenefluoride-co-trifluoroethylene (PVDF-TrFE), and other ferroelectric polymers. The piezoelectric sensor 140 may be a differential sensor (e.g., a differential PVDF sensor). In some cases, the piezoelectric sensor 140 may be cut or patterned into a serpentine, curved, or arcuate shape, which may make the piezoelectric material even more flexible and/or help the piezoelectric sensor 140 better match the acoustic impedance of human skin. A serpentine, curved, or arcuate shape can help to reduce the strain experienced by a material.

The flexible nature of the piezoelectric sensor 140 may allow the piezoelectric sensor 140 to be large enough to wrap around a substantial portion of the circumference of the user's limb (e.g., 25%, 50%, or more of the circumference of the user's limb). This may allow the blood pressure measurement device 100 to be placed in more locations and rotational positions on the user's limb 103, while still allowing the device to perform reliable measurements.

The piezoelectric sensor 140 may be able to detect multiple signals at multiple locations along the limb 103. For example, the piezoelectric sensor 140 may detect signals at different locations along the limb 103. The processing unit may be able to analyze an output signal of the piezoelectric sensor 140 to determine multiple waveforms, each of which corresponds to a biological parameter or blood pressure. The processing unit may determine which of the signals to use to determine blood pressure or other biological parameters. In some cases, for example, one or more signals may include more noise than other signals, in which case one or more signals with less noise may be used to determine blood pressure or other biological parameters. Similarly, one or more signals may be stronger (e.g., have higher amplitudes) than other signals, in which case one or more stronger signals may be used to determine blood pressure or other biological parameters. In some cases, the blood pressure measurement device 100 may include multiple piezoelectric sensors 140 for detecting signals, as described in more detail below with respect to FIGS. 7 and 8.

Figure 5A:
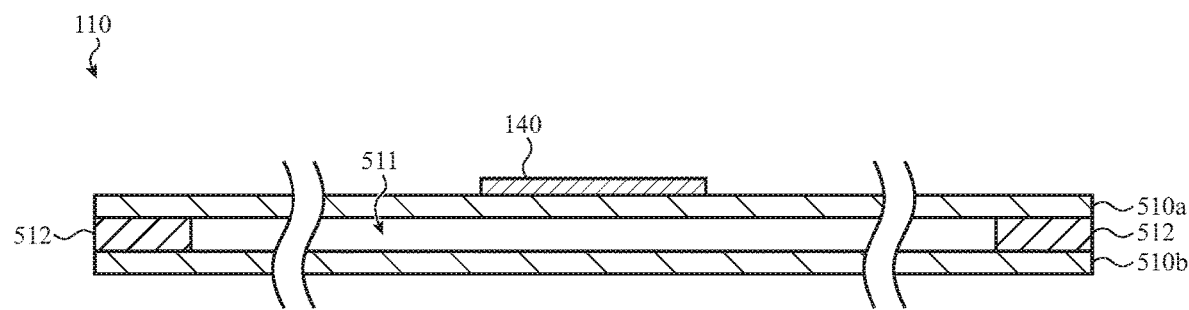
FIGS. 5A and 5B illustrate cross-section views of the example blood pressure measurement device of FIG. 1, taken through section line 5-5 of FIG. 4.
Figure 5B:
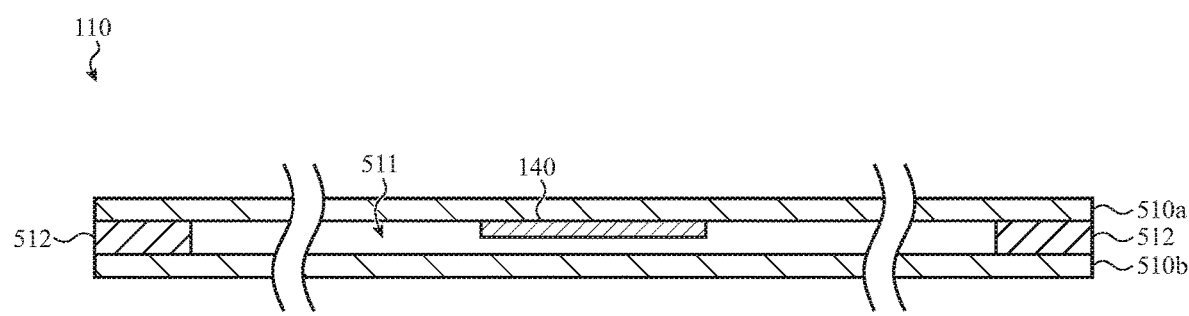

In some cases, the bladder section 110 may include two or more flexible layers that are attached or otherwise coupled to one another to form the inflatable bladder. FIGS. 5A and 5B illustrate cross-section views of the example blood pressure measurement device 100, taken through section line 5-5 of FIG. 4. As shown in FIGS. 5A and 5B, the bladder section 110 may include a first flexible layer 510a and a second flexible layer 510b. A peripheral region of the first flexible layer 510a may be coupled to a peripheral region of the second flexible layer 510b, for example by an attachment mechanism 512, to form an inflatable interior volume 511 of the inflatable bladder. The first flexible layer 510a may be configured to contact the user's limb (e.g., arm).

The first and second flexible layers 510a, 510b may be formed of any suitable flexible material(s) that are capable of being deformed as the inflatable bladder inflates and/or as the cuff 105 is wrapped around a user's limb. Example materials include fabrics (e.g., fabric including one or more of nylon, polyester, cotton, or the like), flexible polymers (e.g., polyurethane, PVC, polyethylene, polyimide, cellulose, etc.), rubbers, synthetic rubbers, fiber reinforced materials, composite materials, and the like. The attachment mechanism 512 may be an adhesive or other fastening component, or it may be the result of ultrasonic welding or other attachment processes. In some cases, the bladder section 110 includes a continuous sheet of material that forms the first and second flexible layers 510a, 510b.

The piezoelectric sensor 140 may be coupled to the first flexible layer 510a or the second flexible layer 510b. FIG. 5A shows the piezoelectric sensor 140 coupled to the first flexible layer 510a along a first surface of the first flexible layer that faces away from the inflatable bladder and the second flexible layer and toward a user's limb when the blood pressure measurement device 100 is worn by the user. FIG. 5B shows the piezoelectric sensor 140 coupled to the first flexible layer 510a along a second surface of the first flexible layer that faces toward the inflatable bladder and the second flexible layer 510b. As shown in FIG. 5B, the piezoelectric sensor 140 may be positioned between the first flexible layer 510a and the second flexible layer 510b. In some cases, the piezoelectric sensor 140 may be positioned between sheets of material or other components that make up the first flexible layer 510a or the second flexible layer 510b.

The piezoelectric sensor 140 may be coupled to the bladder section 110 in any suitable way. The piezoelectric sensor 140 may be attached to the first flexible layer 510a or the second flexible layer 510b, for example using adhesive or other techniques or materials. In some cases, the piezoelectric sensor 140 is integrated with the first flexible layer 510a or the second flexible layer 510b. For example, one or more layers that make up the piezoelectric sensor 140 may be printed onto or within the first flexible layer 510a or the second flexible layer 510b.

Figure 6:
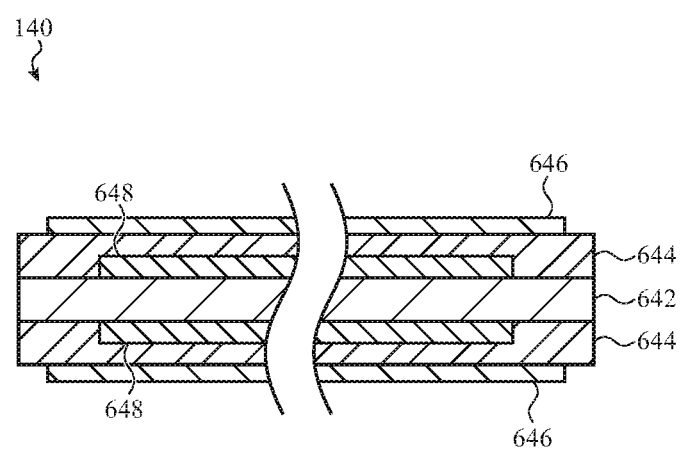
FIG. 6 is an example detail cross-section view of the piezoelectric sensor shown in FIG. 5.

FIG. 6 is an example detail cross-section view of the piezoelectric sensor 140 shown in FIG. 5. The piezoelectric sensor 140 may include a sensor layer 642. As noted above, the sensor layer may be formed of or include a flexible piezoelectric material. Examples of flexible piezoelectric materials include polyvinylidene fluoride (PVDF), polyvinylidenefluoride-co-trifluoroethylene (PVDF-TrFE), and other ferroelectric polymers. The piezoelectric sensor 140 may further include one or more electrode layers 648 abutting or otherwise adjacent to the sensor layer 642. The electrode layers 648 may electrically couple the sensor layer 642 to the processing unit or another circuit or component of the device 100. The electrode layers 648 may carry signals corresponding to inputs detected by the sensor layer 642. The electrode layers 648 may be coupled to a differential sensor (e.g., a differential sense amplifier).

The electrode layers 648 may be formed by depositing (e.g., printing, attaching with a conductive adhesive) a metallic film or other material on a surface of the sensor layer 642. In some cases, the electrode layers 648 may include silver for more precise detection of piezoelectric charge generated by the sensor layer 642. Other examples of electrode materials include silver (e.g., silver/silver sulfate, silver/silver chloride), copper (copper/copper sulfate, copper nickel), mercury (calomel), aluminum, gold (AgNW), and the like.

The piezoelectric sensor 140 may include shielding layers 646 positioned adjacent to on one or more sides of the sensor layer 642 and/or the electrode layers 648. The shielding layers 646 may prevent or reduce signal interference related to the sensor layer 642 and/or the electrode layers 644. The shielding layers 646 may be formed of or include a metallic film or other material. Examples of shielding layer materials include silver (e.g., silver/silver sulfate, silver/silver chloride), copper (copper/copper sulfate, copper nickel), mercury (calomel), aluminum, gold (AgNW), and the like.

The piezoelectric sensor 140 may include additional or alternative layers. The piezoelectric sensor 140 may include one or more insulating layers 644. The insulating layers 644 may at least partially encapsulate or otherwise surround the electrode layers 648 and/or the sensor layer 642. The insulating layers 644 may electrically insulate the electrode layers 644 and/or otherwise protect or stiffen the piezoelectric sensor 140. The insulating layers 644 may be formed of any suitable material or combination of materials, including polymers, foams, and the like. In some cases, the insulating layers 644 may be formed of or include polyethylene terephthalate (PET).

In some cases, the piezoelectric sensor 140 includes one or more adhesive layers between layers of the piezoelectric sensor and/or between the piezoelectric sensor and other device components. The adhesive layers may include pressure-sensitive adhesive or another type of adhesive and may attach one or more portions of the piezoelectric sensor 140 and/or the device 100 together.

Preferably, all of the layers stacked with the sensor layer 642, and any components, such as electrodes or shields, are compliant and have a modulus of elasticity that is similar to or lower than (and preferably significantly lower than) the modulus of elasticity of the sensor layer 642, so that there is a low shear strain between layers, and so that the other components and layers do not interfere with stretch or contraction of the sensor layer 642 and do not significantly alter the sensing capability of the sensor layer 642.

Figure 7:
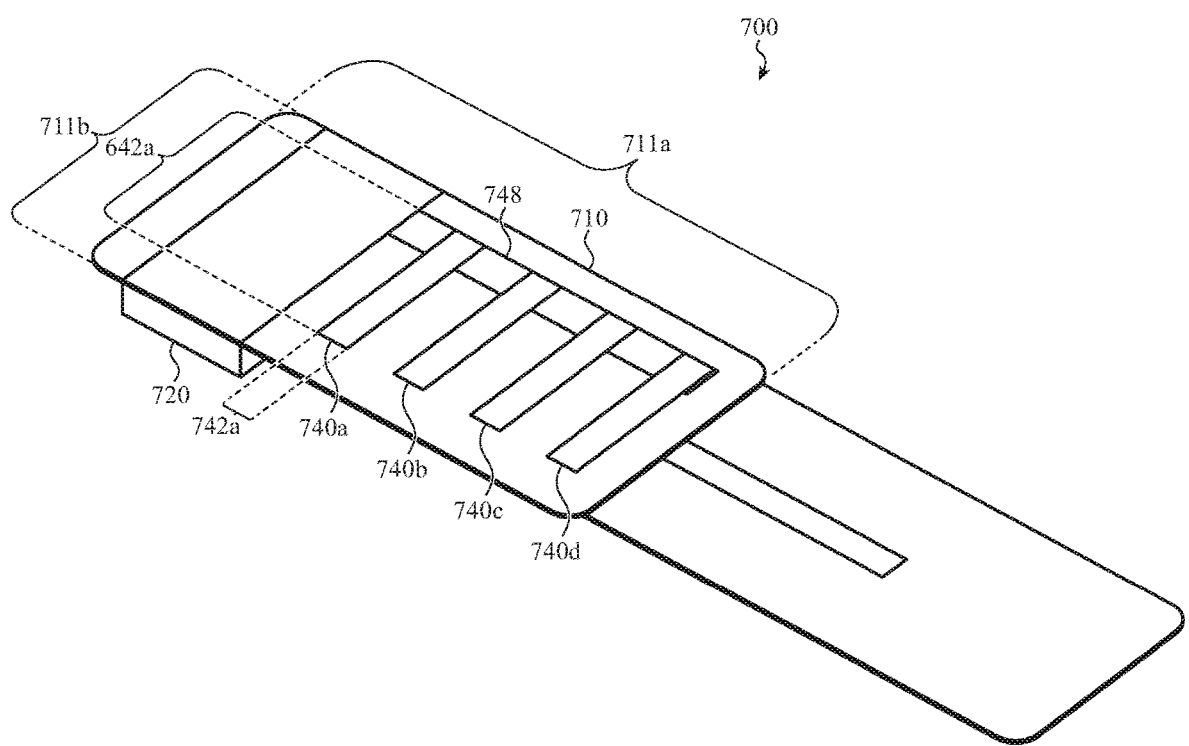
FIG. 7 illustrates an example blood pressure monitoring device with multiple piezoelectric sensors.

As noted above, the blood pressure monitoring devices described herein may include multiple piezoelectric sensors. FIG. 7 illustrates an example blood pressure monitoring device 700 with multiple piezoelectric sensors 740a-d. The blood pressure monitoring device 700 may be similar to the blood pressure monitoring device 100, and may have similar components and provide similar functionality, including a control module 720.

The piezoelectric sensors 740a-d may form an array of sensors. Each piezoelectric sensor 740a-d may define a length 742a and a width 742b. The length 742a of the piezoelectric sensors 740a-d may extend perpendicular to a length 711a and parallel to a width 711b of the bladder section of the blood pressure monitoring device 700. Each piezoelectric sensor 740a-d may extend longitudinally along a limb of a user. The array of sensors may extend at least partially around a user's limb. In various embodiments, the piezoelectric sensors 740a-d may share common components. For example, one or more electrode layers, shielding layers, insulating layers, and the like may form a one or more connectors (e.g., connector 748) that operably couple one or more of the piezoelectric sensors 740a-d to other piezoelectric sensors, the control module 720, or the like.

The piezoelectric sensors 740a-d shown in FIG. 7 may be substantially the same size and dimensions and may be oriented substantially the same way as one another. In various embodiments, the blood pressure monitoring devices described herein may have different sizes or dimensions, and may be oriented or positioned differently from one another.

Figure 8:
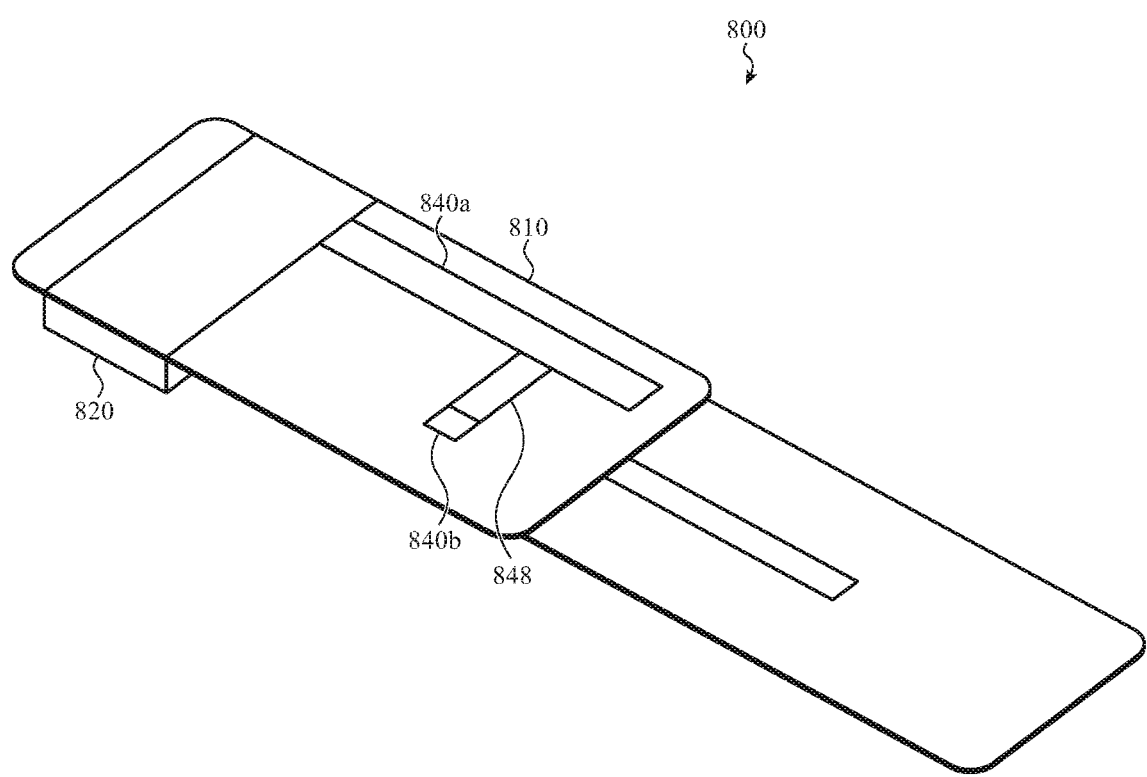
FIG. 8 illustrates an example blood pressure monitoring device with multiple piezoelectric sensors.

FIG. 8 illustrates an example blood pressure monitoring device 800 with multiple piezoelectric sensors 840a, 840b. The blood pressure monitoring device 800 may be similar to the blood pressure monitoring devices 100, 800, and may have similar components and provide similar functionality, including a control module 820 and a connector 848. The piezoelectric sensors 840a, 840b may be shaped differently from one another. For example, the piezoelectric sensor 840a may be similarly shaped and/or positioned to the piezoelectric sensor 140 of the blood pressure monitoring device 100, and the piezoelectric sensor 840b may have a square shape.

As noted above, one or more sensors of the blood pressure monitoring devices described herein (e.g., the capacitive sensor 180, the piezoelectric sensor 140, etc.) may be used to determine one or more operational states of the blood pressure monitoring device 800. The operational states of the blood pressure monitoring devices described herein may include an on-arm or off-arm state, a tightness of the blood pressure monitoring device around a user's limb, and the like. An output signal of the sensors of the blood pressure monitoring devices described herein (e.g., the capacitive sensor 180, the piezoelectric sensor 140, etc.) may correspond to the operational state of the blood pressure monitoring device.

Figure 9:
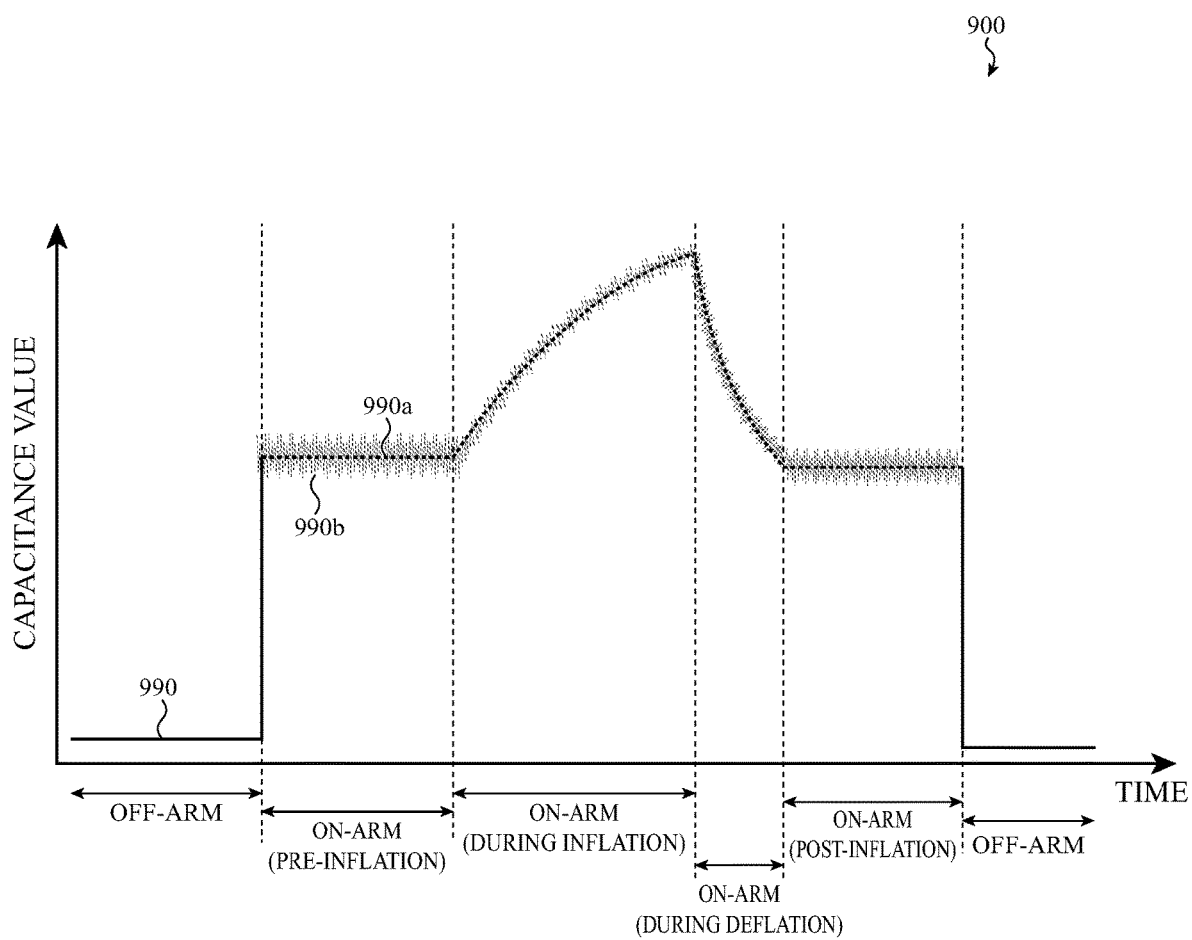
FIG. 9 illustrates an example chart of capacitance values output by a sensor mapped to example operational states of a blood pressure monitoring device.

FIG. 9 illustrates an example chart 900 of capacitance values of an output signal 990 output by a capacitive sensor (e.g., capacitive sensor 180) mapped to example operational states of a blood pressure monitoring device (e.g., blood pressure monitoring device 100). A processing unit (e.g., processing unit 124) of the blood pressure monitoring device may determine an operational state using the output signal (e.g., a capacitance value) of the sensor.

As shown in FIG. 9, a relatively low capacitance value 990 may correspond to an off-arm state. A higher, constant capacitance value may correspond to an on-arm, and perhaps uninflated (pre-inflation or post-inflation), state. A gradual increase in the capacitance value may correspond to an inflation operation (e.g., inflating an inflatable bladder of the blood pressure monitoring device). A gradual decrease in the capacitance value may correspond to a deflation sequence (e.g., deflating the inflatable bladder of the blood pressure monitoring device). The operational state may also be determined based on a previous operational state (e.g., an immediately previous operational state) and/or one or more future operational states (e.g., an immediately following operational state).

The processing unit of the blood pressure monitoring device may determine, from the output signal 990 of the sensor, that the blood pressure monitoring device is on a user's limb. The processing unit may use signals detected by the sensor to determine biological signals while the device is in the on-arm state. In response to determining that the device is in the on-arm state, the processing unit may cause a pump of the blood pressure monitoring device to inflate an inflatable bladder to tighten the device around the user's limb. Upon determining from an output signal of the sensor that the inflatable bladder is sufficiently inflated (e.g., that an inflation process is complete), the processing unit may receive signals from one or more piezoelectric sensors, which may be used to determine a blood pressure measurement and/or one or more biological parameters.

The processing unit may determine a tightness of the blood pressure monitoring device on the user's limb using an output signal of a sensor (e.g., capacitive sensor 180). If the tightness is below a threshold tightness, the processing unit may cause the pump to further inflate the inflatable bladder. If the tightness is at or above the threshold tightness, the processing unit may cause a piezoelectric sensor to detect a signal, for example during a deflation sequence, for use in determining a blood pressure measurement.

As shown in FIG. 9, when the blood pressure monitoring device is in an on-arm state, the output signal 990 may include a first (DC) component 990*a* corresponding to the tightness of the blood pressure monitoring device on the user's limb and a second (AC) component 990*b* corresponding to blood flow (e.g., pulsatile blood flow) through the limb. In some cases, the processing unit may filter the output signal 990 to isolate the first component 990*a* and/or the second component 990*b*. The first component 990*a* may be used to determine the state and/or tightness of the blood pressure monitoring device. The second component 990*b* may be used to determine one or more biological parameters.

In various embodiments, blood pressure measurements, biological parameters, and/or operational states may be determined using a variety of sensor types, including but not limited to, strain sensors, capacitive sensors, ultrasonic sensors, resistive sensors, optical sensors, piezoelectric sensors, and thermal sensors.

Figure 10:
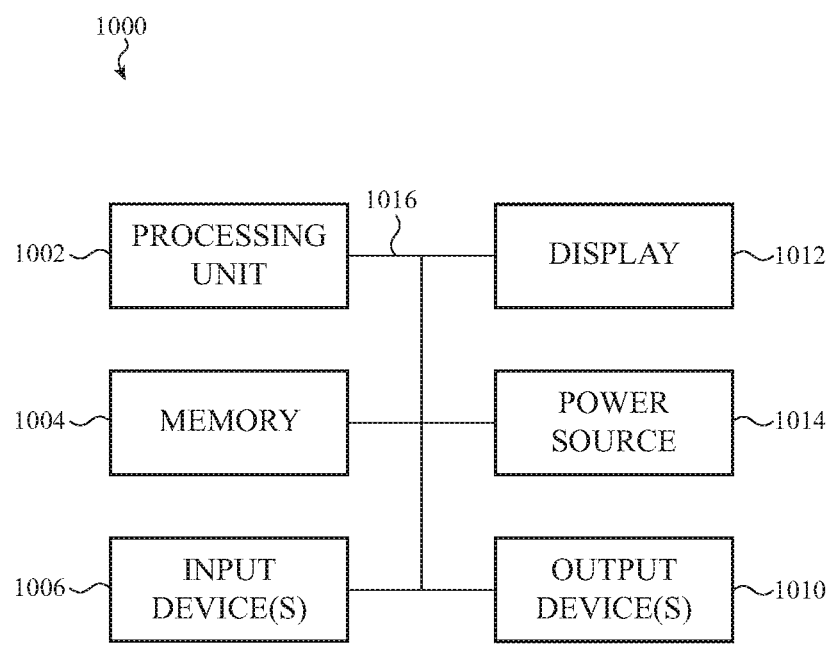
FIG. 10 illustrates a sample electrical block diagram of an electronic device, such as a blood pressure measurement device.

FIG. 10 illustrates a sample electrical block diagram of an electronic device 1000, such as a blood pressure measurement device. The electronic device may in some cases take the form of any of the blood pressure measurement devices described with reference to FIGS. 1-9, or other portable or wearable electronic devices. The electronic device 1000 can include a display 1012 (e.g., a light-emitting display), a processing unit 1002, a power source 1014, a memory 1004 or storage device, an input device 1006 (e.g., a piezoelectric sensor, a biological parameter sensor, and the like), and an output device 1010.

The processing unit 1002 can control some or all of the operations of the electronic device 1000. The processing unit 1002 can communicate, either directly or indirectly, with some or all of the components of the electronic device 1000. For example, a system bus or other communication mechanism 1016 can provide communication between the processing unit 1002, the power source 1014, the memory 1004, the input device(s) 1006, and the output device(s) 1010. In some cases, the electronic device 1000 may only include enough processing power to capture measurements and transmit them (wirelessly or over one or more wires) to a device with a processing unit that can analyze/display the measurements, perform computations of biometric data derived therefrom, and the like.

The processing unit 1002 can be implemented as any electronic device capable of processing, receiving, or transmitting data or instructions. For example, the processing unit 1002 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 1000 can be controlled by multiple processing units. For example, select components of the electronic device 1000 (e.g., an input device 1006) may be controlled by a first processing unit and other components of the electronic device 1000 (e.g., the display 1012) may be controlled by a second processing unit, where the first and second processing units may or may not be in communication with each other. In some cases, the processing unit 1002 may determine a biological parameter of a user of the electronic device.

The power source 1014 can be implemented with any device capable of providing energy to the electronic device 1000. For example, the power source 1014 may be one or more batteries or rechargeable batteries. Additionally or alternatively, the power source 1014 can be a power connector or power cord that connects the electronic device 1000 to another power source, such as a wall outlet.

The memory 1004 can store electronic data that can be used by the electronic device 1000. For example, the memory 1004 can store electrical data or content such as, for example, audio and video files, documents and applications, device settings and user preferences, timing signals, control signals, and data structures or databases. The memory 1004 can be configured as any type of memory. By way of example only, the memory 1004 can be implemented as random access memory, read-only memory, Flash memory, removable memory, other types of storage elements, or combinations of such devices.

In various embodiments, the display 1012 provides a graphical output, for example associated with an operating system, user interface, and/or applications of the electronic device 1000. In one embodiment, the display 1012 includes one or more sensors and is configured as a touch-sensitive (e.g., single-touch, multi-touch) and/or force-sensitive display to receive inputs from a user. For example, the display 1012 may be integrated with a touch sensor (e.g., a capacitive touch sensor) and/or a force sensor to provide a touch- and/or force-sensitive display. The display 1012 is operably coupled to the processing unit 1002 of the electronic device 1000.

The display 1012 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 1012 is positioned beneath and viewable through a cover that forms at least a portion of an enclosure of the electronic device 1000.

In various embodiments, the input devices 1006 may include any suitable components for detecting inputs. Examples of input devices 1006 include piezoelectric sensors, biological parameter sensors, audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 1006 may be configured to detect one or more particular types of input and provide a signal (e.g., an input signal) corresponding to the detected input. The signal may be provided, for example, to the processing unit 1002.

As discussed above, in some cases, the input device(s) 1006 include a touch sensor (e.g., a capacitive touch sensor) integrated with the display 1012 to provide a touch-sensitive display. Similarly, in some cases, the input device(s) 1006 include a force sensor (e.g., a capacitive force sensor) integrated with the display 1012 to provide a force-sensitive display.

The output devices 1010 may include any suitable components for providing outputs. Examples of output devices 1010 include audio output devices (e.g., speakers), visual output devices (e.g., lights or displays), tactile output devices (e.g., haptic output devices), communication devices (e.g., wired or wireless communication devices), and so on, or some combination thereof. Each output device 1010 may be configured to receive one or more signals (e.g., an output signal provided by the processing unit 1002) and provide an output corresponding to the signal.

In some cases, input devices 1006 and output devices 1010 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 1002 may be operably coupled to the input devices 1006 and the output devices 1010. The processing unit 1002 may be adapted to exchange signals with the input devices 1006 and the output devices 1010. For example, the processing unit 1002 may receive an input signal from an input device 1006 that corresponds to an input detected by the input device 1006. The processing unit 1002 may interpret the received input signal to determine whether to provide and/or change one or more outputs in response to the input signal. The processing unit 1002 may then send an output signal to one or more of the output devices 1010, to provide and/or change outputs as appropriate.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

As described above, one aspect of the present technology is determining blood pressure measurements, biological parameters, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

What is claimed is:

1. A blood pressure measurement device comprising:
   a cuff configured to extend around an arm of a user, the cuff comprising an inflatable bladder;
   a pump;
   a piezoelectric sensor coupled to the cuff;
   a capacitive sensor coupled to the inflatable bladder; and
   a processing unit operably coupled to the piezoelectric sensor and the capacitive sensor, the processing unit configured to;
      determine, at least in part based on a signal generated by the capacitive sensor, that the blood pressure measurement device is in an on-arm state;
      in response to determining the blood pressure measurement device is in the on-arm state, cause the pump to inflate the inflatable bladder; and
      after the inflatable bladder is inflated to occlude a blood vessel of the user, while the bladder is deflating, and based at least in part on a signal generated by the piezoelectric sensor and responsive to blood flow in the arm of the user, determine a blood pressure of the user.

2. The blood pressure measurement device of claim 1, wherein:
   the inflatable bladder comprises:
      a first flexible layer configured to contact the arm of the user; and
      a second flexible layer, a peripheral region of the second flexible layer coupled to a peripheral region of the first flexible layer to form an inflatable interior volume; and
   the piezoelectric sensor is coupled to the first flexible layer.

3. The blood pressure measurement device of claim 2, wherein the piezoelectric sensor is positioned between the first flexible layer and the second flexible layer.

4. The blood pressure measurement device of claim 2, wherein the piezoelectric sensor is coupled to a surface of the first flexible layer that faces away from the second flexible layer.

5. The blood pressure measurement device of claim 1, wherein the piezoelectric sensor is a differential polyvinylidene fluoride (PVDF) sensor.

6. The blood pressure measurement device of claim 1, wherein:
   the signal generated by the piezoelectric sensor comprises an oscillometric waveform; and
   determining the blood pressure of the user comprises analyzing the oscillometric waveform to determine at least one of a systolic blood pressure, a diastolic blood pressure, or a mean arterial pressure.

7. The blood pressure measurement device of claim 6, wherein:
   the signal generated by the piezoelectric sensor further comprises a biological waveform;
   the processing unit is further configured to:
      filter the signal generated by the piezoelectric sensor to isolate the biological waveform; and
      analyze the biological waveform to determine at least one of a ballistocardiogram, a heart rate, a heart rate variability, or a pulse wave velocity.

8. The blood pressure measurement device of claim 1, wherein the capacitive sensor is according to a mutual-capacitive sensing technique or a self-capacitive sensing technique.

9. A blood pressure measurement device comprising:
a cuff comprising an inflatable bladder;
a processing unit configured to:
- in accordance with determining that the blood pressure measurement device is in an on-arm state, cause the inflatable bladder to inflate to an inflated state, the cuff configured to occlude an artery of a user when the inflatable bladder is in the inflated state, the on-arm state of the blood pressure measurement device determined based on an output signal of a capacitive sensor; and
- cause the inflatable bladder to deflate during a deflation sequence; and a differential polyvinylidene fluoride (PVDF) sensor coupled to the inflatable bladder and configured to output a signal during the deflation sequence, the signal generated by the PVDF sensor corresponds to blood flow through the artery; wherein:
the processing unit is further configured to:
- filter the signal generated by the PVDF sensor to isolate an oscillometric waveform and a biological waveform;
- analyze the oscillometric waveform to determine at least one of a systolic blood pressure, a diastolic blood pressure, or a mean arterial pressure; and
- analyze the biological waveform to determine a biological parameter of the user.

10. The blood pressure measurement device of claim 9, wherein:
the output signal of the capacitive sensor corresponds to a pressure applied to an arm of the user by the cuff; and
analyzing the oscillometric waveform comprises correlating a maximum oscillation of the oscillometric waveform to the pressure applied to the arm of the user by the cuff to determine the mean arterial pressure.

11. The blood pressure measurement device of claim 9, wherein the blood pressure measurement device further comprises a pump configured to inflate the inflatable bladder.

12. The blood pressure measurement device of claim 9, wherein the biological parameter comprises at least one of a ballistocardiogram, a heart rate, a heart rate variability, or a pulse wave velocity.

13. The blood pressure measurement device of claim 9, wherein:
the signal generated by the PVDF sensor further comprises a pressure waveform corresponding to a pressure applied to an arm of the user by the cuff;
the processing unit is further configured to filter the signal generated by the PVDF sensor to isolate the pressure waveform; and
analyzing the oscillometric waveform comprises correlating a maximum oscillation of the oscillometric waveform to the pressure applied to the arm of the user by the cuff to determine the mean arterial pressure.

14. The blood pressure measurement device of claim 9, wherein the capacitive sensor is according to a mutual-capacitive sensing technique or a self-capacitive sensing technique.

* * * * *